United States Patent [19]

Isler et al.

[11] Patent Number: 5,447,953
[45] Date of Patent: Sep. 5, 1995

[54] BIOMASSES TO TREAT NON-HUMAN ANIMALS

[75] Inventors: Dorothea Isler, Basel; Walter Rehm, Riehen; Erich Widmer, Münchenstein, all of Switzerland

[73] Assignee: Hoffmann-La Roche Inc., Nutley, N.J.

[21] Appl. No.: 261,644

[22] Filed: Jun. 17, 1994

Related U.S. Application Data

[63] Continuation of Ser. No. 76,662, Jun. 14, 1993, abandoned.

[30] Foreign Application Priority Data

Jun. 24, 1992 [CH] Switzerland ............... 1990/92

[51] Int. Cl.⁶ .................. A61K 35/00; A61K 31/335
[52] U.S. Cl. .................. 514/449; 424/115; 514/909
[58] Field of Search .............. 514/909, 449; 424/115

[56] References Cited

U.S. PATENT DOCUMENTS

| | | | |
|---|---|---|---|
| 3,462,275 | 8/1969 | Bellamy | 99/9 |
| 4,189,438 | 2/1980 | Umezawa et al. | 260/343.9 |
| 4,202,824 | 5/1980 | Umezawa et al. | 260/343.9 |
| 4,211,765 | 7/1980 | Johnson et al. | 424/78 |
| 4,218,443 | 8/1980 | Comai et al. | 424/181 |
| 4,302,450 | 11/1981 | Comai et al. | 424/181 |
| 4,598,089 | 7/1986 | Hadvary et al. | 514/449 |
| 4,931,463 | 6/1990 | Barbier et al. | 514/422 |
| 5,063,210 | 11/1991 | Lange, III et al. | 514/54 |
| 5,260,310 | 11/1993 | Derungs et al. | 514/449 |

FOREIGN PATENT DOCUMENTS

| | | |
|---|---|---|
| 9171228 | 2/1990 | Australia . |
| 129748 | 6/1984 | European Pat. Off. . |
| 185359 | 12/1985 | European Pat. Off. . |
| 444482 | 2/1991 | European Pat. Off. . |
| 4040874 | 6/1991 | Germany . |

OTHER PUBLICATIONS

Hendrick, J. A., et al., *The Journal of Nutrition*, vol. 122(2), pp. 269–277 (Feb., 1992).
Derwent Abstract No. AN-91-194523/27. (1993).

*Primary Examiner*—Marianne M. Cintins
*Assistant Examiner*—T. J. Criares
*Attorney, Agent, or Firm*—George M. Gould; George W. Johnston; Robert A. Silverman

[57] ABSTRACT

The use of biomasses obtained in the fermentative production of lipase inhibitors, especially lipstatin, for the preparation of foodstuffs, feedstuffs, food additives, feed additives, feed supplements, medicinal feed premixes or medicaments for oral administration, are described.

4 Claims, No Drawings

BIOMASSES TO TREAT NON-HUMAN ANIMALS

This is a continuation of application Ser. No. 08/076,662 filed Jun. 14, 1993, now abandoned.

BRIEF SUMMARY OF THE INVENTION

The invention relates to the use of biomasses obtained in the fermentative production of lipase inhibitors, especially lipstatin, for the preparation of foodstuffs, feedstuffs, food additives, feed additives, feed supplements, medicinal feed premixes or medicaments for oral administration. The invention also relates to foodstuffs, feedstuffs, food additives, feed additives, feed supplements, medicinal feed premixes or medicaments for oral administration containing a biomass obtained in the fermentative production of lipase inhibitors, especially lipstatin, and, if desired, added water-insoluble crude fibers. The invention is further related to foodstuffs, feedstuffs, food additives, feed additives, feed supplements, medicinal feed premixes or medicaments for oral administration containing one or more lipase inhibitors, especially lipstatin or tetrahydrolipstatin, and added water-insoluble crude fibers, whereby the lipase inhibitor(s) is/are present in pure form and/or in the form of the biomass(es) obtained in the fermentative production of the lipase inhibitor(s), especially of lipstatin.

DETAILED DESCRIPTION OF THE INVENTION

The invention relates to the use of biomasses obtained in the fermentative production of lipase inhibitors, especially lipstatin, for the preparation of foodstuffs, feedstuffs, food additives, feed additives, feed supplements, medicinal feed premixes or medicaments for oral administration. The invention also relates to foodstuffs, feedstuffs, food additives, feed additives, feed supplements, medicinal feed premixes or medicaments for oral administration containing a biomass obtained in the fermentative production of lipase inhibitors, especially lipstatin, and, if desired, added water-insoluble crude fibers. The invention is further related to foodstuffs, feedstuffs, food additives, feed additives, feed supplements, medicinal feed premixes or medicaments for oral administration containing one or more lipase inhibitors, especially lipstatin or tetrahydrolipstatin, and added water-insoluble crude fibers, whereby the lipase inhibitor(s) is/are present in pure form and/or in the form of the biomass(es) obtained in the fermentative production of the lipase inhibitor(s), especially of lipstatin.

Animals have certain taste preferences and prefer one specific feed to another. Provided that an animal is trained to a specific feed through hunger, it takes this feed when the hunger is sufficiently great. However, when the situation permits, an animal, especially a dog or a cat, attempts to consume feed which is pleasant and, where the feed is present in excess, it becomes overweight. This naturally occurs to an increasing extent in industrial countries.

An essential factor for the acceptance of a feed, primarily in the case of carnivores, is a determined fat content in the feed. From experience, a reduction of fat in the feed leads, at least in carnivores, to acceptance problems. Accordingly, for example, the conversion of dogs to a so-called diet feed with reduced fat content is associated with difficulties. Moreover, animals require an adequate volume of feed for satiation.

The ideal feed for dogs and, respectively, cats consists of a mixture of albumin, carbohydrates and fat as well as minerals, trace elements and vitamins, which preserves the ideal weight of the animal. Since animals tend to consume feed in an amount above the natural requirement when it tastes good to them, about one third of all dogs and cats are today adipose. The adiposity can be prevented if a dog or a cat receives a feed which has the following properties:

- the feed must be acceptable, that is, taste acceptable to the animal;
- it must have the required volume and must satiate;
- the absorption of essential nutrients should be guaranteed;
- it should not cause excessive weight increase leading to an adiposity; and
- the feces should be formed such that it can be readily collected.

For the absorption of fat found in feed, the primary ester bonds of triglycerides are cleaved by pancreas lipase into free fatty acids, as well as di- and monoglycerides. These substances are then absorbed and utilized by the animal. Lipase inhibitors inhibit to a substantial extent the cleavage of fat in feed and thus the absorption and utilization of fat in feed. Triglycerides are excreted in unchanged form.

Lipase inhibitors, such as lipstatin (LST) and analogues thereof, such as tetrahydrolipstatin (THL) and N-formyl-L-leucine (S)-1-[[(2S,3S)-3-ethyl-4-oxo-2-oxetanyl]methyl]octadecyl ester (LOC), which are used in the scope of the invention, are described in EPA 129 748, EPA 185 359 and EPA 444 482. Additionally, lipase inhibitors are esterastin and its derivatives which are described in U.S. Pat. No. 4,189,438 and U.S. Pat. No. 4,202,824. Examples of biomasses or fermentation cakes obtained in the fermentative production of lipase inhibitors, such as lipstatin or esterastin, are described in EPA 129 748 and U.S. Pat. No. 4,189,438.

It will be appreciated that the addition of the lipase inhibitor to the feed is dependent on the fat content of the feed. The production of an ideal feed for dogs and cats is possible by the addition of 0.1 to 100 mg of lipase inhibitor per g of fat, preferably of 1 to 50 mg of lipase inhibitor per g of fat, to the feed.

The lipase-inhibiting substances can be added as feed additives, as set forth, for example, in the EEC feed guidelines, to the daily feed, especially to the daily sole feed. Such a feed would then make a conventional diet feed for the prevention or therapy of adiposity superfluous. They can also be added as an additive to a diet feed which contains, for example, a low salt diet. The incorporation in a special diet feed which is used for the prevention or therapy of adiposity is also possible.

The lipase-inhibiting substances can also be used as a feed supplement or as a medicament for oral administration by presentation in the form of tablets, capsules, granulates, powders, drinking water additives as single ingredients or in combination or mixtures with other ingredients of feed supplements or medicaments for oral administration.

In order to use lipase inhibitors in the form of feed medicaments, as defined, for example, in EEC guidelines, the lipase inhibitors can also be added to medicinal feed premixes.

The activity of the lipase inhibitor is improved by the addition of water-insoluble crude fibers. Examples of such crude fibers are microcrystalline cellulose, for example, AVICEL, wheat bran and oat bran. After the addition of the crude fibers, the crude fiber content in the feed to the fat content of the feed should stand in a minimal weight ratio of 1/1.5. An increase in the crude fiber content is of course possible in order to achieve an additional increase in the activity of the lipase inhibitor. An optimal addition of crude fibers has a weight ratio to feed fat of ½ or ⅓, that is, the crude fiber content should be about double to three times the fat content of the feed. Apart from the increased prevention of fat absorption by the addition of crude fibers, the consistency of the feces of the animals is also maintained.

Chemically-produced pure lipase-inhibiting substance or microbiologically-produced material, as is the case, for example, with lipstatin, can be used for all of the above purposes.

An especially advantageous preparation for use in animals is the application of the fermentation cake (the biomass) in pure, semi-solid or dried form. The fermentation cake also contains valuable albumin and fat in addition to lipstatin. From its composition, the fermentation cake can also be considered to be a natural feed containing a lipase inhibitor. By the direct addition of the fermentation cake to the feed, other usually added nutrients can be dispensed with, for example, albumin in the form of soya meal and animal or vegetable fat.

The pure substance or the fermentation cake can be used as follows:

a) as a feed additive to the daily feed or to diet feed of animals, especially of dogs and cats, in order to maintain the ideal weight of the animals or to-prevent and treat adiposity in these animals,
b) as a feed supplement or medicament for oral administration or as an additive to feed supplements or to medicaments for oral administration, in combination with other ingredients of feed supplements or medicaments,
c) as a additive to feed medicines or medicinal feed medicine premixes.

The following benefits result from this use:

a) A substantial prevention of fat absorption in the gastrointestinal tract. The fat absorption, depending on the dosage of the lipase inhibitor and the added crude fibers, is between 1 and 100% of the amount of fat consumed with the feed, but preferably about to 40 to 70% of the fat in the feed.
b) Prevention and treatment of adiposity, primarily in dogs and cats, with the possibility remaining that the animals become satiated and do not turn to other feeds in order to satisfy residual hunger.
c) Prevention and treatment of adiposity by feeding a feed or a diet feed which contains the lipase-inhibiting substances and which feeds the animal pleasurably, that is, complete acceptance is maintained such that a more or less compulsory training to a different feed is superfluous.
d) Saving of feed constituents of vegetable and/or animal origin.

The above also applies mutatis mutandis for humans.

Further, it has to be mentioned that substances which inhibit the absorption of fat in the feed of animals can be used for the formation of low-fat musculature in animals, especially of animals reared for fattening.

EXAMPLE 1

Demonstration of the activity of a lipase inhibitor using tetrahydrolipstatin (THL) by way of example on the fat absorption from the feed and the influence of cellulose on the THL activity in dogs.

Female dogs aged 7 to 15 years and having a body weight between 13 and 22 kg are divided into 2 groups each of 6 animals. The animals are fed with a standard dog food. The animals have free access to drinking water.

The animals are given a test meal on the day of the test. This test meal contains as feed components 7.5% protein, 19% carbohydrate, 6% fat, 1.6% minerals, 45% water and 20% ballast materials. The fat of the feed consists of 58% olive oil treated with C-14 triolein. The remaining fat is composed predominantly of saturated fatty acids. The lipase inhibitor THL and optionally the cellulose are admixed with the test diet in the doses given in the tables.

The absorption of the fat administered orally with the test diet was measured on the basis of the recovered radioactivity in the feces of the dogs. The difference between the orally-administered amount of C-14 labelled triolein and the radioactivity found in the feces within three days after intake of the test meal is considered to be absorbed fat. The absorbed amount is given as a percentage of the administered amount. The lower the absorption is, that is, the lower the percentage is, then the greater is the activity of the lipase inhibitor.

The results are recorded in Table 1.

TAB. 1

Activity of THL alone and THL + cellulose on fat absorption in dogs

|  | Control | Group 1 | | Group 2 | |
| --- | --- | --- | --- | --- | --- |
| Test meal in g | 420 | 340 | 420 | 340 | 420 |
| Total amount of fat in g/test meal | 26 | 26 | 26 | 26 | 26 |
| Cellulose in g/test meal | 80 | 0 | 80 | 0 | 80 |
| THL dose | | | | | |
| in mg/test meal | 0 | 20 | 20 | 50 | 50 |
| in mg/kg body wt. | 0 | 1.5 | 1.5 | 4 | 4 |
| Triolein absorption in % of the applied dose | 100 | 70 | 48 | 63 | 28 |

The blood plasma concentrations with respect to total glycerol of dogs which received test diet of 50 mg THL+80 g cellulose have been compared in Table 2 with those of a control without THL, but with cellulose.

TAB. 2

Comparison of the blood plasma concentrations after a test meal with 50 mg THL and 80 g cellulose and a test meal with 80 g cellulose without THL.

| | Total plasma glycerol (mmol/l ± SEM) | |
| --- | --- | --- |
| Time of measurement | Control (80 g cellulose) | Lipase inhibitor (50 mg THL + 80 g cellulose) |
| Before administration (starting value) | 0.6 ± 0.05 | 0.7 ± 0.07 |
| 3 Hrs. after administration | 1.3 ± 0.17 | 0.5 ± 0.02 |
| 7 Hrs. after administration | 0.8 ± 0.07 | 0.9 ± 0.13 |

Discussion of the results:

From Table 1, it will be evident that the lipase inhibitor THL even as a sole additive to the test meal leads to a reduction of 30 to 37%, depending of the dose, of the absorption of fat contained in the feed. The activity of the lipase inhibitor is considerably increased when cellulose is added to the test meal together with the lipase inhibitor. In the Example, after the addition of cellulose an increase from about 30-37% to about 52-70% of the inhibition of the absorption of the administered radioactively labelled fat in the feed was possible.

The results recorded in Table 1 are confirmed by the measurement of the plasma glycerol level in dogs which received a test meal with 80 g cellulose with or without 50 mg of THL. Three (3) hours after the intake of the test meal, the glycerol concentrations in the plasma of the dogs without THL were considerably increased, which can be due to the absorption of fat administered in the feed, while no increase occurred in the group with THL, which confirmed the inhibition of the absorption of fat in the feed. The slight increase in the absorption, 7 hours postprandial, must be seen in connection with the attenuated fat absorption of 28%.

The feces of the dogs was solid and formed in the case of animals which received cellulose alone or in combination with THL, while it was rather pulp-like in the case of animals which received THL without cellulose.

EXAMPLE 2

Determination of the activity of a lipase inhibitor using lipstatin (LST, chemically pure or as a component of a fermentation cake) by way of example, on the fat absorption from the feed in the case of mice and dogs and the influence of cellulose on the activity was undertaken.

The Example is conducted in 2 parts. Part a) describes a test with mice, the results of which can be confirmed by a test with dogs (part b). In this part of the test, the influence of cellulose on the activity of the lipase inhibitor is also investigated.

Microbiologically-produced lipstatin (LST) is used as the lipase inhibitor in both parts of the test. LST is equivalent as a chemically pure substance with LST as a component of a fermentation cake produced according to Example 4 of EP 129 748. The content of LST in the cake was determined at 4 g of LST per kg of fresh fermentation cake using conventional analytical methods.

A Weender analysis for the determination of the nutrient content of animal feed gave the following values for the fermentation cake:

Dry substance content of the fermentation cake: 192 g/kg

| Dry substance content per kg: | |
|---|---|
| Crude ash | 31.4 g |
| Crude protein | 251.6 g |
| Crude fiber | 9.1 g |
| Crude fat | 499.4 g |
| N-free extract material | 208.5 g | a) Mouse test Comparison of chemically pure LST with LST as a component of a fermentation cake.

Pure LST or the dried fermentation cake was suspended in 5% gum arabic/5% lactose preparation, conventional in pharmacological tests, and administered orally to animals, which had been pre-fasted for 24 hours, in an amount of 10 ml/kg per mouse immediately after a liquid test meal. The test meal contained 2.5% starch, 24% glucose, 12% lactose and 7.6% olive oil labelled with C-14 triolein. The amount of pure LST or cake is adjusted such that the doses set forth in Table 3 are guaranteed. Thereafter, the mice received a conventional standard feed.

The calculation of the absorbed fat in the feed was carried out as described in Example 1.

The results of the test are reported in Table 3 in which the LST dose is calculated per mg/kg body weight. The values are average values calculated from measurements on, in each case, 3 mice per test.

TAB. 3

| Activity of pure LST and LST in a fermentation cake on the fat absorption using 3 mice per dose was determined. | | |
|---|---|---|
| LST dose | Triolein absorption in % per dose administered | |
| in mg/kg | pure LST | LST in the fermentation cake |
| 2.7 | nd | 83 |
| 5.0 | 69 | nd |
| 15 | 52 | nd |
| 18.0 | nd | 54 |
| 50.0 | 41 | nd | nd = not determined b) Dog Test

This test was carried out analogously to Example 1. The lipase inhibitor was LST in the fermentation cake described in part a) of this Example. This cake was admixed with the test meal for dogs containing an additional 80 g of cellulose per test meal, as described in Example 1.

The results are reported in Table 4.

TAB. 4

| Activity of LST as a component of a fermentation cake alone or in combination with cellulose on fat absorption in dogs was determined. | | | | |
|---|---|---|---|---|
| LST dose | | Number of | Triolein absorption in % of the orally administered amount | |
| mg/kg body wt. | mg/meal | animals N | LST alone | LST + cellulose |
| 1.9 | 20 | 2 | nd | 94 |
| 4.3 | 50 | 4 | 86 | 68 |
| 13.9 | 150 | 4 | 69 | 38 |
| 41.0 | 460 | 4 | 33 | 14 |
| | ID$_{50}$ in mg/meal | | 240 | 95 |

The differences are statistically significant in the t-Test pair comparison with $p<0.05$.

The results from the dog test (b) confirm, above all the results achieved in test a) with mice, that LST is a very active lipase inhibitor even when it is present in a fermentation cake. This was surprising, because it has to be appreciated that the inhibitor is not liberated from the cells in which it is formed, as is the case, for example, with other natural products, such as vitamins. The troublesome and expensive isolation of the LST from the fermentation cake can thus be dispensed with, without taking into consideration a loss of activity.

The potency of the lipase inhibitor is increased by a factor of 3 in the presence of cellulose, as already described in Example 1, and can also be proved by the results of part b) of Example 2.

EXAMPLE 3

Determination of the activity of a lipase inhibitor using the lipstatin derivative LOC defined above, by way of example, on the fat absorption from the feed in the case of single and repeated administration to mice was undertaken.

3 Albino mice weighing 25 g were used per dose in the test.

The mice received over several days a so-called fat diet in which the fat content was adjusted such that the mice received 23.4 g of fat per kg body wt. per day. The mice were fed with this feed for 8 days. On days 3 to 6 of the test C-14, labelled triolein and LOC in a dose of 50 mg/kg body weight were admixed with this feed. The feces of the mice was collected at intervals of 24 hours from days 4 to 8 of the test and evaluated according to the guidelines given in Example 1.

The control animals each received the test diet without the LOC active substance.

The absorption of the orally administered fat was measured as in Examples 1 and 2.

The results of the test are reported in Table 5:
Tab. 5: Activity of LOC after 1 and, respectively, 4 days administration on the fat absorption in mice was determined.

| LOC dose | Triolein absorption in % of the amount given orally (± SDM) | |
|---|---|---|
| | 1st day | 4th day |
| Control (no LOC) | 100 | 100 |
| 50 mg/kg body wt. | 26 ± 4 | 26 ± 3 |

From the Table it will be evident that, even after administration of medication for several days, the activity of a lipase inhibitor is unchanged, that is, the absorption inhibition of the fat in the feed remains undiminished.

EXAMPLE 4

Good diet with reduced protein and salt content for dogs (the amount corresponds to a daily ration for a dog weighing 10 kg):

| | |
|---|---|
| 200 g | chicken liver or minced meat |
| 10 g | butter |
| 100 g | crude rice |
| 60 g | wheat bran |
| 4 g | dicalcium phosphate |
| 2.5 g | vitamin mixture; vitamin A and E should be present in sufficient amounts and in non-esterified form |
| 50 to 100 g | lipstatin-containing fermentation cake (4 g lipstatin/kg cake) |

The meat is fried in the butter and mixed with the rice (boiled with a small amount of salt). Subsequently, the lipstatin-containing fermentation cake, the crude fiber, mineral and vitamin mixture are added and the mixture is appropriately preserved, for example, in a 500 g preserving jar. Where only a low salt diet is desired, the amount of meat can be increased and the amount of rice can be correspondingly lowered.

EXAMPLE 5

Simple mixture using lipstatin-containing fermentation cake as a feed additive:

| | |
|---|---|
| 800 g | canned dog food (75% water, 8–13% protein, 4–7% fat) |
| 200 g | canned dog food (15–20% water, 19–22% protein, 5–15% fat) |
| 80 g | wheat bran |
| 100 g | lipstatin-containing fermentation cake (4 g lipstatin/kg cake) |

The lipstatin fermentation cake is incorporated with the wheat bran into the meal so that a slurry results.

The amount produced corresponds to a daily ration for a dog weighing 20 kg and is suitably given in 2 portions.

A sufficient provision of vitamins A and E is guaranteed by the administration of adequate doses 3 hours before or after the meal.

We claim:

1. A method of treating adiposity comprising administering to a non-human animal in need of such treatment a biomass comprising a lipase inhibitor, wherein the biomass is obtained by a process consisting of fermenting a fermentation broth comprising a microorganism which produces the lipase inhibitor and separating the biomass from the fermented broth, wherein the biomass so obtained is administered in an effective amount for treating adiposity.

2. The method of claim 1, wherein the lipase inhibitor is lipstatin.

3. The method of claim 1, wherein the lipase inhibitor is esterastin.

4. The method of claim 1, comprising administering to the animal a feedstuff, feed additive, feed supplement, medicinal feed premix, or orally administered medicament, comprising the biomass.

* * * * *